United States Patent
Meznaric et al.

(10) Patent No.: US 10,595,723 B2
(45) Date of Patent: Mar. 24, 2020

(54) MEASURING METHOD

(71) Applicant: Haag-Streit AG, Koeniz (CH)

(72) Inventors: André Meznaric, Koeniz (CH);
Bernhard Von Waldkirch, Bern (CH);
Christian Schlaeppi, Bern (CH);
Christian Zoss, Belp (CH); Ernst Rindlisbacher, Boll (CH); Joerg Breitenstein, Zollikofen (CH); Kaspar Baltzer, Bern (CH); Lucio Robledo, Bern (CH); Peter Stalder, Brittnau (CH); Silja Kiriyanthan, Liebefeld (CH)

(73) Assignee: HAAG-STREIT AG, Koeniz (CH)

( * ) Notice: Subject to any disclaimer, the term of this patent is extended or adjusted under 35 U.S.C. 154(b) by 0 days.

(21) Appl. No.: 14/937,402

(22) Filed: Nov. 10, 2015

(65) Prior Publication Data
US 2016/0128565 A1  May 12, 2016

(30) Foreign Application Priority Data
Nov. 12, 2014 (EP) .................................. 14405080

(51) Int. Cl.
*A61B 3/107* (2006.01)
*A61B 3/113* (2006.01)
*A61B 3/10* (2006.01)
*G01B 9/02* (2006.01)

(52) U.S. Cl.
CPC .............. *A61B 3/107* (2013.01); *A61B 3/102* (2013.01); *A61B 3/1005* (2013.01); *A61B 3/113* (2013.01);
(Continued)

(58) Field of Classification Search
CPC ......... A61B 3/04; A61B 3/1015; A61B 3/103; A61B 3/14; A61B 3/152; A61B 3/1225;
(Continued)

(56) References Cited

U.S. PATENT DOCUMENTS 4,871,904 A * 10/1989 Metlitsky ........... G06K 7/10633
235/462.38
5,988,508 A  11/1999 Bridgelall et al.
(Continued)

FOREIGN PATENT DOCUMENTS

DE    199 12 428 A1  10/2000
EP    1 975 550 A1   10/2008
(Continued)

OTHER PUBLICATIONS

Karnowski et al., "Corneal topography with high-speed swept source OCT in clinical examination", Biomedical Optics Express, Optical Society of America, vol. 2, No. 9, Sep. 1, 2011, pp. 2709-2720.
(Continued)

*Primary Examiner* — Jie Lei
(74) *Attorney, Agent, or Firm* — Birch, Stewart, Kolasch & Birch, LLP

(57) ABSTRACT

In a method for registering measurement points on a body, in particular on an eye, measurement points are registered along a trajectory on a surface of the body, in particular a curved surface of the body, for determining an axial length profile, by way of a measurement beam. Here, a minimum radius of curvature of the trajectory is at least ½, preferably at least ⅕, particularly preferably at least ⅓ of a radius of a circumference of the surface.

33 Claims, 4 Drawing Sheets

(52) U.S. Cl.
CPC ..... *G01B 9/02077* (2013.01); *G01B 9/02091* (2013.01); *G01B 2290/65* (2013.01)

(58) Field of Classification Search
CPC ....... A61B 3/107; A61B 3/1005; A61B 3/113; A61B 3/102; A61B 3/10; A61B 5/0059; A61B 5/0066; G01B 9/02; G01B 9/02077; G01B 9/02091; G01B 2290/65; G06K 7/10693; G06K 7/10881; G06K 7/10871
USPC ....... 351/212, 211, 210, 205, 208, 221, 236, 351/246; 356/479; 235/462.4, 462.36, 235/462.37, 462.38, 462.39; 600/425, 600/476
See application file for complete search history.

(56) References Cited

U.S. PATENT DOCUMENTS

| | | | |
|---|---|---|---|
| 2006/0170930 A1* | 8/2006 | Li | A61B 5/0059 356/479 |
| 2010/0142780 A1 | 6/2010 | Yasuno et al. | |
| 2012/0119105 A1 | 5/2012 | Iwata | |

FOREIGN PATENT DOCUMENTS

| | | |
|---|---|---|
| EP | 2 417 903 A1 | 2/2012 |
| JP | 2007-130403 A | 5/2007 |
| JP | 2010-046216 A | 3/2010 |
| JP | 2013-166072 A | 8/2013 |
| WO | WO 2007/091991 A2 | 8/2007 |
| WO | WO 2012/066631 A1 | 5/2012 |
| WO | WO 2014/059331 A1 | 4/2014 |

OTHER PUBLICATIONS

McNabb et al., "Distributed scanning volumetric SDOCT for motion corrected corneal biometry", Biomedical Optics Express, Optical Society of America, vol. 3, No. 9, Sep. 1, 2012, pp. 2050-2065.

Park et al., "Forward imaging OCT endoscopic catheter based on MEMS lens scanning", Optics Letters, Optical Society of America, vol. 37, No. 13, Jul. 1, 2012, pp. 2673-2675.

Tuma et al., "High-speed multiresolution scanning probe microscopy based on Lissajous scan trajectories", IOP Publishing, Nanotechnology, vol. 23, No. 185501, 2012, pp. 1-9.

* cited by examiner

MEASURING METHOD

TECHNICAL FIELD

The invention relates to a method for registering measurement points on a body, wherein measurement points are registered along a trajectory on a surface of the body by way of a measurement beam.

PRIOR ART

Various methods and devices which can be used to measure the eye are known in ophthalmology. By way of example, optical interferometry lends itself as a noninvasive, contactless and precise process. Furthermore, there are a number of other processes, e.g. ultrasonic biometry, (placido) corneal topography, Scheimpflug cameras, split microscopes, etc. Typically, such examinations on the eye are implemented using an interferometer. By way of example, OCTs (optical coherence tomography scanners) are used as interferometers, which scan the eye point-by-point in the lateral direction and, in the process, register stray light profiles (axial profiles) of the eye along the optical beam.

In the article "Distributed scanning volumetric SCOCT for motion corrected corneal biometry" (1 Sep. 2012, volume 3, number 9, Biomedical Optics Express), Ryan P. McNabb disclose a scanning method which can register topographies of an eye using DSOCT (distributed scanning OCT). Here, movements of the eye are established by means of SDOCT (spectral domain OCT) and included in the measurement. The eye is scanned along a trajectory which, in a projection, covers a circular disk. The trajectory starts in the edge region and extends along a first straight line through the center of the circle. Subsequently, the measurement beam is deflected at the opposite edge region in such a way that it extends back through the circle center point along a second straight line offset from the first straight line by 90° in order, once again, to be deflected in the same direction at the edge region. This method is repeated until the start point is reached again.

In the publication dated 1 Sep. 2011, volume 2, No. 9, Biomedical Optics Express, Karol Karnowski et al. disclose a scanning method in which a measurement beam is displaced along straight lines arranged at right angles to one another, i.e. along a grid.

EP 1 975 550 A1 discloses an optical system for measuring an eye using OCT. Firstly, a spiral form and, secondly, lines extending in parallel are disclosed as a trajectory.

EP 2 417 903 discloses further concentric rings, and grids and parallel lines as trajectory forms, over which a measurement beam passes.

The known methods are disadvantageous in that the measurements take a relatively long period of time. Due to the relatively long measurement duration, there is an increased risk of the measurement results being influenced by eye movements of the patient, as a result of which only imprecise measurement results can be achieved.

Essential requirements for measuring, particularly when measuring the eye, are, firstly, a short overall duration of the measurement and a high resolution, i.e. a large coverage of the surface to be measured.

SUMMARY OF THE INVENTION

The object of the invention is to develop a method, which is part of the technical field set forth at the outset, for registering measurement points on a body which can be carried out particularly quickly at a high resolution.

The solution of object is defined by the features of claim 1. In accordance with the invention, a minimum radius of curvature of the trajectory is at least ½, preferably at least ⅕, particularly preferably at least ⅓ of a radius of a circumference of the surface.

The invention is furthermore based on a device for carrying out this method. To this end, the device preferably comprises one of the measurement apparatuses mentioned below, preferably an interferometer, particular preferably an OCT instrument. The measurement apparatus preferably comprises a controller enabling a guidance of a measurement beam in accordance with the aforementioned method. Such controllers are sufficiently well known to a person skilled in the art.

In principle, the measurement method is based on a length measurement, in particular an axial length measurement in the Z-direction (see below), particularly preferably an axial scattering profile (a so-called A-scan) along the beam direction. However, the measurement method can also be available as a different direct or indirect measurement. A time-of-flight measurement, more particularly using e.g. a laser, or acoustically by means of an echo solder can be provided as indirect measurement. The lengths can be determined directly by confocal or interferometric methods. By way of example, OCT can be used as an interferometric measurement method. A person skilled in the art is also aware of further suitable measurement techniques.

Below, X, Y and Z coordinates are used as a three-dimensional orthogonal system. The trajectory is preferably considered along an XY-plane and the measurement beam has the Z-direction in at least one measurement direction, in particular in the direction of the center point of the circumference. From this location, the measurement beam can be moved in parallel, i.e. maintain the Z-direction, or else be swiveled about one angle in the X-direction and about a second angle in the Y-direction. Furthermore, the change in location can also be achieved by a combination of these variants. To the extent that nothing else is mentioned, the preferred first variant is assumed below, without this constituting a restriction to one of the variants. To this end, provision can be made of telecentric optical units, in which a beam offset can be implemented in parallel. The length measurement relates to the Z-axis or the direction of the measurement beam, wherein changes in the refractive index along the measurement axis may lead to refractive effects, which are registered as an axial scattering profile. Methods for geometric correction and conversions of the measured lengths are well known to a person skilled in the art.

The trajectory described in more detail below is respectively understood as a plane projection in an XY-plane, which intersects the body to be measured or which has a small distance from the body to be measured. In practice, the trajectory can deviate from this description, depending on the body to be measured. By way of example, if points are registered along a trajectory at regular intervals by means of the measurement beam, these points only lie at constant distances on the body to be measured if the body is a plane that is parallel to the plane projection. However, if this trajectory is projected onto a spherical cap for example, measurement points adjacent in time near the center lie closer to one another than measurement points adjacent in time in the edge region of the spherical cap.

In principle, the body to be measured can be arbitrary. Depending on the embodiment of the body, i.e. depending on the material and size of the body, or depending on whether this is a living being, the measurement method explained below can be selected accordingly or adapted and parameterized. However, the method is preferably used for measuring or determining measurement points on a human or animal eye, particularly preferably on the human eye, which may optionally have contact lenses or intraocular lenses. Here, the boundary layers of the eye (of the cornea, of the lens, of the retina) are preferably measured. These boundary layers can generally be described approximately by spherical segments in the central region. The points of intersection of the measurement beam with a boundary layer therefore lie approximately on a spherical cap. The same applies when measuring artificial bodies with approximately spherical interfaces, such as contact lenses or intraocular lenses. Hence, the body to be measured preferably has approximately the shape of a spherical segment and the trajectory in practice preferably extends along a spherical cap—however, the trajectories are in each case considered as XY-projections in the plane (see below).

When applying the method to an eye the curved surface is preferably a surface region, in particular the cornea, or a region of a deeper layer in the eye. However, the curved surface can also be provided by an inserted contact lens or intraocular lens.

An axial length profile or A-scan should be understood to mean a profile of the body along the z-axis or along the beam direction. A B-scan is understood to mean an axial profile along a straight cut through the body, which is composed of individual measurement points and distances. The axial length profile can be combined to form a three-dimensional model of the body or a cut through the body, in particular the eye. However, the data can also be used in a different way, for example for simulating a beam path, a correction lens or the like.

The degree of coverage is that portion of the surface to be measured in which the distance from any desired point to the closest measurement point does not exceed a critical value. A degree of coverage of 100% is usually required for measuring the topography of the eye, wherein the surface to be measured should have at least a diameter of 7.5 mm and the critical distance should be 0.5 mm. However, depending on the requirements, for example when realizing shorter measurement times, it is also possible to use smaller degrees of coverage or smaller measurement surfaces. The surfaces and distances relate to the xy-plane, in which the trajectory is defined.

The radius of curvature of the trajectory is presently determined on the basis of the plane projection of the trajectory in the XY-plane. In the case of a parameterized curve f(t)=(x(t), y(t)), the radius of curvature r is defined as follows:

$$r = \left| \frac{(x'(t)^2 + y'(t)^2)^{\frac{3}{2}}}{x'(t) \cdot y''(t) - x''(t) \cdot y'(t)} \right|$$

To the extent that nothing else is mentioned, the trajectory is defined below in relation to the XY-plane as a two-dimensional curve. However, it is clear to a person skilled in the art that the trajectory in the application as a projection on a body typically constitutes a three-dimensional curve in space, which is distorted in relation to the trajectory. However, since this spatial curve depends both on the trajectory form and on the body form and therefore is able to vary over a large range, this is not discussed in any more detail.

Moreover, the trajectory need not necessarily follow a function definition in a mathematically exact manner. Preferably, the trajectory has a form which lies on the above-described trajectory or one of the above-described trajectories, at least for the individual measurement points. In this case, the functions or forms are finally only defined by an interpolation of the measurement points. However, in practice the measurement points can also deviate slightly from the trajectory. By way of example, the mean deviation from the trajectory can be less than 5%, preferably less than 1% of the diameter of the circumference of the surface to be measured, depending on the number of measurement points and the size of the object.

By selecting the minimum radius of curvature of the trajectory to be at least 1/7, preferably at least 1/5, particularly preferably at least 1/3 of a radius of a circumference of the surface over the whole course of the trajectory, the measurement beam can be displaced particularly quickly without exposing parts of the device, in particular a beam deflection unit or a scanner, to large accelerations. In the case of known trajectories, there usually is a problem in that quick changes of direction need to be undertaken. However, quick changes in direction cannot be carried out with an arbitrary speed. The deceleration and the subsequent acceleration of the movement of the measurement beam cause time delays, which slow down the measurement method as a whole. A consequence of the time delay in turn is that the measurement results can be substantially disturbed by movements of the patient. The longer such a measurement takes, the greater is also the probability that the patient blinks and the measurement method even needs be aborted and restarted under certain circumstances.

The novel trajectory with the relatively large radii of curvature in relation to the surface to be measured now renders it possible to carry out a measurement method which can be carried out quickly relative to the number of measurement points such that movements of the body or of the eye are only able to falsify the measurement result to a lesser extent. However, the radius of curvature is also selected to be sufficiently small so that the surface to be measured can be sufficiently covered in the case of a relatively short path length of the trajectory such that the trajectory can have a sufficiently large degree of coverage.

A problem which may exist when measuring spherical caps is that the distances to the spherical cap along the trajectory in the plane projection experience smaller changes near the center than in the edge region in the case of regular measurement point distributions. Expressed differently, the distances on the spherical cap are no longer constant in the case of constant measurement point distances in the plane projection, but rather increase in the radial direction from the center of the spherical cap. However, large changes in distance along the beam direction (Z-axis) between sequentially registered measurement points lead to losses in the signal contrast, particularly in the case of interferometric measurements (S. Yun et al., Opt. Expr. 12(13), 2977 (2004)). It is therefore particularly advantageous if the edge region of the plane projection of the measurement point distribution has a higher measurement point density along the trajectory than a region near the center when measuring a spherical cap, e.g. when measuring an eye. What this achieves is that the changes in the distance along the trajectory are sufficiently small and hence the signal contrast remains sufficiently high.

Preferably, the trajectory therefore has a large radius of curvature in the edge region of the surface to be measured. Hence, an advantage arising here is that smaller distance changes along the trajectory emerge in the edge region, particularly when measuring spherical caps, and so the regions of the spherical cap with the greatest gradient (i.e. the edge region of the spherical cap) can be measured more exactly.

In variants, the region of the trajectory with the maximum radius of curvature can also lie near the center, in the center itself or in an intermediate region between the edge region and the center. In general, the ideal trajectory conforms to the requirements on the measurement resolution; thus, the exact form of the outer region of the spherical cap may be less important in certain circumstances, as a result of which the large radii of curvature can rather be selected to be near the center.

Preferably, at least 90%, preferably at least 95%, particularly preferably the whole of the trajectory extends within the circumference. As a result, the trajectory can be used substantially completely for registering the measurement points, as a result of which the overall time duration of the measurement can be reduced.

In variants, relatively large portions of the path length of the trajectory can also lie outside of the surface to be measured. By way of example, only at least 80%, 70% of the path length, or less, may be allotted to the surface to be measured. Depending on the size of the surface to be measured, the path length lying outside of the surface can likewise vary. Under certain circumstances, it may be advantageous for particularly small surfaces if a relatively large portion of the path lengths lies outside of the surface, for example at least 50% or at least 75%.

Here, the surface conforms to the largest surface to be considered for determining the measurement points. Under certain circumstances, various portions of the surface can be evaluated, wherein the surface can be considered a union of the portions.

Preferably, the trajectory has a maximum radius of curvature which is less than the radius of the circumference of the surface, in particular over more than 50%, preferably over more than 75%, particularly preferably over a whole path length of the trajectory. As a result, overall, it is possible to form a trajectory which, overall, has relatively large radii of curvature and therefore can be passed over quickly by a measurement beam.

In variants, the trajectory can also have regions with larger radii of curvature than the circumference of the surface. In particular, the trajectory can also have straight portions with a radius of curvature of infinity.

A consequence of a maximum radius of curvature which exceeds the radius of the circumference is that, in the case of a trajectory lying within the surface, it is therefore also necessary to provide relatively small radii of curvature—provided that a sufficient coverage is intended to be achieved, provision therefore needs to be made for radii of curvature which are less than 50% of the circumferential radius, which in turn has a negative effect on the measurement time.

Preferably, the maximum radius of curvature is less than 99%, preferably less than 95%, more particularly less than 90% of the radius of the circumference. As a result of the whole trajectory comprising a smaller radius of curvature than the circumference, it is possible to achieve a particularly uniform trajectory which makes do without relatively large changes in the curvature and therefore can be passed through particularly quickly by a measurement beam.

In variants, the maximum radius of curvature can reach or exceed the radius of the circumference, as mentioned above.

Preferably, a curvature of the trajectory toward the center of the circumference increases monotonically, more particularly strictly monotonically. A larger measurement point density is achieved as a result of the fact the trajectory has a smaller curvature in the edge region of the surface to be measured than in the region near the center. This is advantageous, particularly in the case of spherical cap-shaped bodies, such as e.g. in the case of an eye, because the measurement point density on the spherical cap can be kept sufficiently high as a result, even in the edge region.

In variants, the radius of curvature can also increase toward the center point of the circumference, particularly if e.g. the region near the center is intended to be measured more exactly on account of the form of the body.

Preferably, the trajectory has a point of intersection which is registered at least twice with a time lag. As a result of this, a movement of the body to be measured can be detected. The movement of the body can thus be filtered from the measurement results such that more precise measurement data can be obtained.

In variants, the trajectory can also have points that are only run through twice.

Preferably, the trajectory has at least two spaced apart points of intersection, wherein, in particular, a point of intersection is registered more than twice with a time lag. As a result of the two spaced apart points of intersection, the detection of the movement of the body can be improved, since, as a result of this, it is possible to identify not only the magnitude but also the sign of the movement. Likewise, it is possible to optimize the movement detection by virtue of a point of intersection being passed through more than twice such that temporal changes in the movement can be detected. In general, it is also possible for more than two spaced apart points of intersection to be present, as a result of which the movement detection can be optimized further; in particular, it is thus possible to detect movements along different directions.

In variants, it is also possible to dispense with the plurality of points of intersection or with points of intersection that are passed through more than twice.

Preferably, the at least two points of intersection have an angle of intersection which is greater than 90° in the plane projection.

In variants, the angles of intersection can also be only 90°.

Preferably, the measurement beam follows a trajectory which has more than two points of intersection, wherein, in the case of k*n points of intersection, respectively n points of intersection lie on respectively one of k concentric rings. Particularly preferably, the trajectory has more than four points of intersection since the trivial solution with two concentric rings or a ring with the two points of intersection is possible in the case of two points of intersection.

To the extent that nothing else is mentioned, the term point of intersection in each case is assumed to be a simple point of intersection, which is passed through exactly twice by the measurement beam. The trajectory can have a point of intersection in the center of the circumference such that, overall, k*n+1 points of intersection would emerge. However, in the present case, the center point of the circumference is not considered to be one of the concentric rings, in particular also for the reason that the latter is generally not present as a simple point of intersection.

In a first case, the trajectory has exactly four points of intersection on a ring or respectively two points of intersection on two concentric rings, in addition to a central point of intersection (as mentioned above, a possibly present point of intersection in the center of the circumference is not counted here).

In a further example, the trajectory has e.g. 40 points of intersection on 5 concentric rings, such that 8 points of intersection come to rest on each ring.

It is clear to a person skilled in the art that any number of points of intersection can be divided into two groups of factors according to the principle of prime factorization and can be assigned, firstly, to the n points of intersection per ring and, secondly, to the k rings. The 40 points of intersection can thus be divided between 2 rings with in each case 20 points of intersection, 4 rings with in each case 10 points of intersection, 8 rings with in each case 5 points of intersection and, mutatis mutandis, with the number of points of intersection and rings interchanged.

In variants, the points of intersection of the trajectory can also be arranged differently. By way of example, respectively n and m points of intersection may lie on alternating rings. Here, for example, n can be a multiple of m, wherein a point of intersection n is passed through more than twice.

Preferably, a distance between two adjacent concentric rings with increasing radius is reduced between the three concentric rings with the largest radii. As a result, the rings close up in the direction of the edge region, as a result of which the points of intersection also lie closer together. Thus, a measurement point density can be increased in the edge region in order to improve the measurement accuracy, particularly in the case of spherical objects such as e.g. an eye. At the same time, the movement of the eye can be detected more exactly since a distance in the Z-direction also changes more markedly in the edge region of the eye in the case of a lateral change in distance in the XY-plane and hence it can be used for detecting the eye location.

In variants, the rings can also have a constant spacing or the spacing can reduce in the direction of the circumferential center.

Preferably, points of intersection between the trajectory and the alternating concentric rings respectively lie on a radially oriented straight line. As a result, the points of intersection can be distributed in an ideal manner over the surface to be measured, particularly if the rings have a smaller distance from one another than two adjacent points of intersection on an individual ring. In the case of a respectively constant number of n points of intersection per ring, there respectively is an offset of the adjacent ring in relation to the points of intersection by an angle of 360/2n degrees in this case.

In variants, the rings can also be offset by an angle of 360/k*n degrees, where k>2. Furthermore, it is possible for k<2, in particular for k=1, such that, in the latter case, a radially oriented straight line, which registers a point of intersection registers a point of intersection on each ring. Finally, the points of intersection can also be ordered differently on the rings or be arranged chaotically.

Preferably, the measurement beam is displaced along the projection of the trajectory with a constant angular speed. As a result, a trajectory that is particularly easy to parameterize and analyze is obtained. Moreover, the latter is easy to calibrate.

In variants, the trajectory can also be passed over by the measurement beam not with a constant angular speed but rather with e.g. a constant path speed or with neither a constant path speed nor a constant angular speed.

Preferably, the measurement points are registered by means of spectral domain OCT (SD-OCT) or swept source OCT (SS-OCT), preferably with a time-constant frequency.

Methods using OCT are well established in ophthalmology since these can be used in scattering objects such as an eye and, in particular, have a relatively high penetration depth with, at the same time, a high axial resolution.

In SD-OCT, use is made of different optical frequencies. The light is dispersed and analyzed by means of a CCD or CMOS sensor. As a result, the whole measurement depth can be obtained with a single measurement. By contrast, in SS-OCT, the optical frequency is periodically tuned and the interference signal is measured in a time-resolved manner. These techniques are sufficiently well known to a person skilled in the art.

In variants, it is also possible to use other techniques for a point-based length measurement or for profile measurement (registering A-scans) (see an interferometer), for example a time-of-flight measurement by means of a laser or the like.

Preferably, the trajectory is given by loops, wherein adjacent loops intersect and wherein, in particular, two adjacent loops respectively have a point of intersection which lies on a circle preferably concentric with a circumference of the surface to be measured. This concentric circle preferably has a radius which is smaller than the circumferential radius. The loops preferably all have a common point of intersection, which preferably lies in the center of the circumference. These common points of intersection can also lie on an arbitrary small concentric circle, wherein the spacing of the measurement points on this circle is less than e.g. 0.5 mm, preferably less than 0.1 mm, particularly preferably less than 0.01 mm. Particularly preferably, this concentric ring has a diameter of less than 0.5 mm, preferably less than 0.1 mm, particularly preferably less than 0.01 mm. As a result, it is possible to achieve a high resolution of the central region of the body in a simple manner. This can be advantageous, particularly when determining a surface form of a layer of the eye in ophthalmology.

The loops are preferably embodied in such a way that three successive measurement points on the loops do not lie on a straight line. Depending on the measurement point density, the criterion, in principle, can also be extended to four or more successive measurement points which do not lie on a straight line.

In variants, the trajectory can also not, or not exclusively, be provided by loops, and so three successive measurement points can lie on a straight line. If the criterion is extended to four, five or more points, it is accordingly possible in variants for a trajectory portion of four, five or more successive measurement points to lie on a straight line. Adjacent loops need not necessarily intersect or the points of intersection need not necessarily lie on a circular ring.

Preferably, the trajectory is defined by two frequencies and a radius, more particularly by exactly two frequencies. As a result, it becomes simpler to calibrate the measurement method. It is possible to place fewer requirements in respect of the frequency response on the scanner.

In variants, it is also possible to use more than two frequencies or more than one radius for defining the trajectory. The trajectory can also have a polygonal or any other definition.

Preferably, the measurement beam follows a curve having the following coordinates:

$$x(t) = r_0 * \sin(\omega_B t) * \cos(\omega_T t)$$

$$y(t) = r_0 * \sin(\omega_B t) * \sin(\omega_T t)$$

where:
$r_0$: radius of the circumference of the scanning pattern
$\omega_B$, $\omega_T$: angular speed
where $r_0$ is the radius of the circumference of the surface to be measured. This function constitutes a trajectory that is particularly simple to calibrate and defined by exactly two frequencies ($\omega_B$ and $\omega_T$) and one radius ($r_0$). A further advantage of this trajectory lies in the fact that the increment in the radial direction decreases toward the outside and hence the signal contrast increases. This is particularly advantageous when measuring an eye since the gradient of the surface of the eye increases away from the center of the eye in the radial direction.

In a particularly preferred embodiment, $\omega_B = 4*2\pi/t_{pattern}$ and $\omega_T = 7*2\pi/t_{pattern}$, where $t_{pattern}$ denotes the duration of the measurement cycle. However, the frequencies can also be selected to be different depending on the size of the area to be measured in the case of an unchanging measurement point density or depending on the desired measurement point density in the case of a constant size of area, e.g. $\omega_B = 4*2\pi/t_{pattern}$ and $\omega_T = 5*2\pi/t_{pattern}$ for relatively small areas or relatively small measurement point densities or $\omega_B = 4*2\pi/t_{pattern}$ and $\omega_T = 11*2\pi/t_{pattern}$ for relatively large areas or relatively large measurement point densities. It is clear to a person skilled in the art that this trajectory can be parameterized as desired; in particular, it is also possible to select non-integer multiples of $2\pi/t_{pattern}$ for the angular frequencies. It is likewise clear to a person skilled in the art that the measurement beam need not follow this function in a mathematically exact manner, but that merely the measurement points need to come to rest on the trajectory. Moreover, the measurement points need not lie exactly on the trajectory, but can preferably merely lie sufficiently close to the trajectory, for example with a distance of less than 5%, preferably less than 1%, particularly preferably less than 0.1% of the diameter of the surface to be measured.

In variants, it is also possible to provide a different function for defining a trajectory. By way of example, the trajectory can be provided by the following coordinate equation of the hypotrochoid:

$$x(t) = (a-b)*\cos(\omega*t) + c*\cos\left(\left(\frac{a-b}{b}\right)*\omega*t\right);$$

$$y(t) = (a-b)*\sin(\omega*t) - c*\sin\left(\left(\frac{a-b}{b}\right)*\omega*t\right)$$

Here, the radius of the circumference of the surface to be measured is given by a−b+c.

In the present case, the hypotrochoid is formed by the course of an arbitrary long, radially aligned "pointer" on an inner circle, wherein the inner circle is rolled within a larger circle. Thus, a denotes the radius of the outer circle, b denotes the radius of the inner circle with the pointer of length c. Consequently, the radius of the circumference of the surface to be measured is given by a−b+c.

In the hypotrochoid form, the center can be left open in a region in the case of suitable parameterization. This is the case if b+c<a. The radius of the inner open circle (if present) is therefore a−(b+c). As a result, it is possible to reach many different points of intersection in the region of the center of the circumference, as a result of which the measurement accuracy in the central region can once again be increased. The radius of the inner circle is preferably kept in such a way that a coverage criterion is met, i.e. the radius can be e.g. 0.25 mm or less.

The radius of the central open region is zero precisely when a−b=c, as a result of which a multiple point of intersection lies in the center. This form is to be preferred if the monitoring or correction of the eye movement is weighted more highly than a higher resolution in the central region of the eye.

A person skilled in the art is aware of arbitrary further variations of trajectories, which likewise only have large radii of curvature and which cover both the center and the edge region with a high resolution.

Preferably, for each measurement point on the trajectory, there is a second measurement point on the same trajectory at a distance of less than 25%, preferably of less than 16% of the radius of the circumference. Particularly preferably, there is at least one measurement point on each circle on the surface to be measured with a radius that is less than 25%, preferably with a radius that is less than 16%, particularly preferably with a radius that is less than 5% of the circumference. As a result, an ideal measurement point density with a sufficient resolution of the body is obtained.

In variants, the distance to the next measurement point can also be restricted differently.

Preferably, for each point within the circumference of the surface, there is a measurement point on the trajectory at a distance of at most 0.5 mm, preferably at most 0.25 mm, particularly preferably at most 0.1 mm. As a result, it is possible to obtain an ideal coverage with measurement points of the surface to be measured, particularly when measuring on the eye.

In variants, a coverage with measurement points of the surface to be measured can also be defined differently. By way of example, provision can be made in a further preferred variant for the measurement point distribution on the surface to be measured to be retained in such a way that a circular disk with a radius of 0.5 mm, preferably of 0.25 mm, particularly preferably of 0.1 mm, coming to rest within the surface to be measured, always covers at least one measurement point, independently of the position thereof.

The invention further relates to a method for approximating a cross section of a body. The measurement points required for the approximation method are preferably implemented using the above-described method for measuring a body.

However, it is also conceivable to establish the measurement points using a different method, in particular by way of conventional measurement methods known to a person skilled in the art.

To this end, in order to approximate the cross section of the body, preferably of an eye, in the region of the cross section of the eye, a subset of registered measurement points, which comprise at least one measurement point at a distance from the cross section, has operations performed thereon in order to approximate the cross section. As a result, it is possible to calculate arbitrary cross sections of the body, without respectively appropriate measurement points needing to be available exactly in the cross section.

Preferably, the subset of the registered measurement points of two sectors with center-point angles of less than 90° arranged in a mirror symmetric manner is in a circumference of a surface to be measured.

In the case of a measurement method with a constant angular speed, it is thus possible to achieve, over the cross section, a substantially constant number of measurement points per cross sectional length portion.

In variants, the sector can also not be delimited by straight lines but rather not expand linearly from the center of the circumference in the radial direction. A weighting that can be applied thereby is that measurement points situated further away from the cross section result in greater unsharpness in the approximation; as a result of this, more measurement points are included in these regions. It is clear to a person skilled in the art that, in principle, any differently formed surface can be used for approximating a cross section. In particular, a cross section can also not extend in a linear fashion but rather, for example, can be embodied in a V-shaped manner, as a "piece of cake" of the object, such that the sphere of influence accordingly comprises two circular sectors, which optionally have an intermediate angle or which contact each other or overlap. The cross section can also have a different profile, e.g. a wave-shaped profile, a polygonal profile such as e.g. a regular polygon, a zigzag-shaped profile, etc.

Further advantageous embodiments and combinations of features of the invention emerge from the following detailed description and the totality of the patent claims.

BRIEF DESCRIPTION OF THE DRAWINGS

In the drawings used to explain the exemplary embodiment.

In principle, the same parts are provided with the same reference sign in the figures.

WAYS OF IMPLEMENTING THE INVENTION

Figure 1:
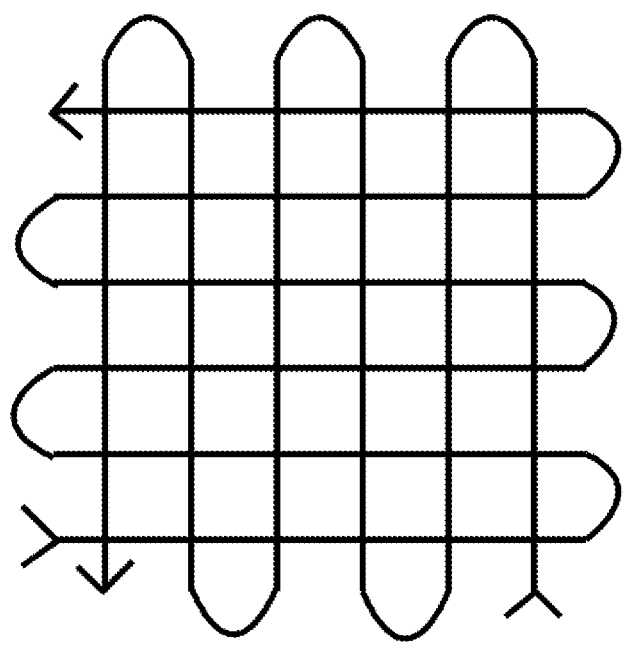
FIG. 1 shows a raster-shaped scanning pattern in accordance with the prior art.

FIG. 1 shows a raster-shaped scanning pattern in accordance with the prior art. The scanning pattern is known, inter alia, from tube televisions, in which the electron beam passes over the screen line-by-line. FIG. 1 shows two equal patterns, which are offset by 90° to one another and overlap one another. Both patterns are traveled over separately. While the straight pieces of the parts of the trajectory can be passed over relatively quickly, there respectively are significant delays in the edge region as a result of the abrupt directional changes. Therefore, this scanning pattern cannot be passed over in a sufficiently efficient manner in terms of time by means of a measurement beam. Moreover, the scanning pattern has the same measurement point density in the edge region as in the center, particularly in the case of a circular or spherical cap-shaped body such as e.g. an eye. Hence, this scanning pattern or this trajectory does not have an ideal embodiment for registering surfaces of an eye.

Figure 2:
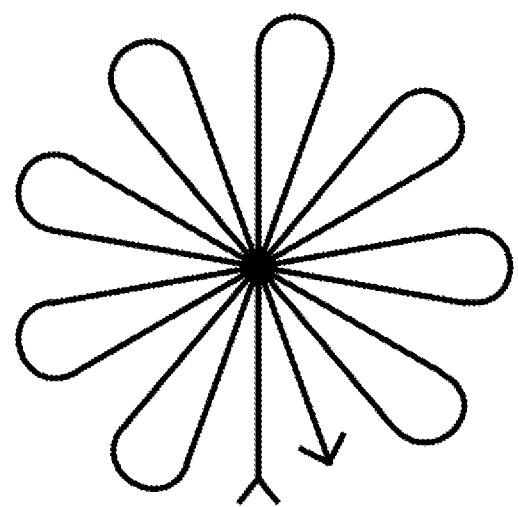
FIG. 2 shows a loop-shaped scanning pattern in accordance with the prior art.

FIG. 2 shows a loop-shaped scanning pattern in accordance with the prior art. This scanning pattern has a plurality of loops formed from the center. Expressed differently, the scanning pattern is provided by straight portions, which pass over the center of the circumference of the surface to be measured at regular angular distances. Respectively at the end of such a straight portion there is the connection to the adjacent portion, e.g. respectively in a clockwise direction, by way of the loop formation. The formed loop ends have a relatively small radius of curvature. The greater the angular distances of the portions are, the larger the radius of curvature becomes at the end of the portion but, on the other hand, the total number of portions reduces simultaneously, as a result of which the measurement point density on the surface to be measured is also reduced. As a result, the two factors of radius of curvature and measurement point density or the maximum distance between two adjacent points are pitted against one another. A further disadvantage lies in the fact that there is a very large increase in density of measurement points in the center, which do not meaningfully serve the evaluation of the surface profile of the body. Optionally, the scanning pattern can be selected to be so large that a large part of the scanning pattern lies outside of the surface to be measured. An advantage thereof would be that the radii of curvature are larger and can be passed through more quickly, but, on the other hand, this would increase the overall path length greatly such that, overall, the measurement duration would be increased.

Figure 3:
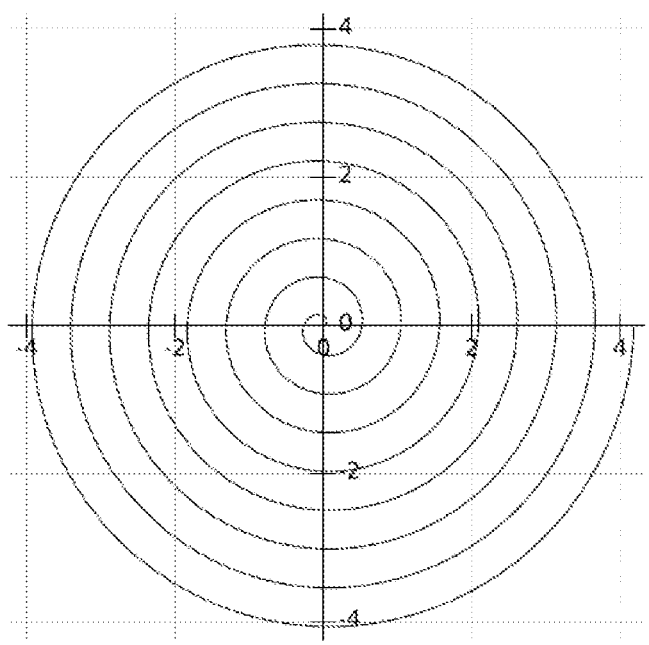
FIG. 3 shows a spiral-shaped scanning pattern in accordance with the prior art.

FIG. 3 shows a spiral-shaped scanning pattern in accordance with the prior art. While the spiral pattern in the edge region has sufficiently large radii of curvature, which could be quickly passed through by a measurement beam, the radius of curvature becomes ever smaller toward the center. However, since the central region is very important, particularly in ophthalmology, this scanning pattern is also disadvantageous in that the central region can only be passed through very slowly or only measured with a low resolution.

In the following FIGS. 4 to 7, four different scanning patterns according to the invention with the general form:

$$x(t)=r_0*\sin(\omega_B t)*\cos(\omega_T t)$$

$$y(t)=r_0*\sin(\omega_B t)*\sin(\omega_T t)$$

are depicted. Here:

$r_0$: radius of the circumference of the scanning pattern $\omega_B$:

$$\omega_B = 2\pi \frac{B}{2t_{pattern}},$$

$\omega_T$:

$$\omega_T = 2\pi \frac{T}{t_{pattern}}.$$

In the following examples, the measurement duration $t_{pattern}$ is 200 ms (milliseconds). It is clear to a person skilled in the art that, in principle, the shortest possible measurement duration is sought after. However, the latter is dependent firstly on the measurement instrument employed and secondly on the number of measurement points.

In the present case, the number of measurement points is 3200 and the measurement frequency (i.e. the rate at which measurement points are registered) is f=16 kHz. Here, equilibrium is sought after, in which the measurement duration is sufficiently short and, simultaneously, the number of measurement points and hence, in the case of a constant surface to be measured, the resolution is sufficiently large. However, furthermore, the measurement frequency is only so large that a sufficient signal strength still emerges for each measurement point, as said signal strength decreases with increasing measurement frequency. Depending on the measurement system, the measurement frequency can be from a few kHz to several MHz. Measurement frequencies in the range from 10 to 200 kHz were found to be worthwhile.

Depending on the employed measurement instrument, the measurement duration and the number of measurement points can also be smaller or larger. Depending on the measurement arrangement, it may be advantageous if the measurement duration is shortened, with the smaller resolution being accepted. On the other hand, it is also possible to increase the number of measurement points to the detriment of the measurement duration.

In the present case, the radius of the surface to be measured is 4 mm. However, this is likewise dependent on the specific requirements and can, in principle, be selected arbitrarily, e.g. 10 mm, 3.5 mm, 1.5 mm and all ranges lying therebetween and outside thereof.

The axial system resolution of the measurement instrument is approximately 4.6 µm in the present case, but it can also be higher or lower.

It is clear to a person skilled in the art that the diameter, the number of measurement points and the measurement time can lie in different ranges.

Finally, it is also clear to a person skilled in the art that the trajectory is not restricted to exactly complying with the graphs formed by the generally specified equations (equations above and below). A trajectory or scanning pattern can also deviate from the mathematically exact form. Thus, for example, the set of points established by the measurement beam can merely approximately correspond to such a function as an interpolation.

Figure 4:
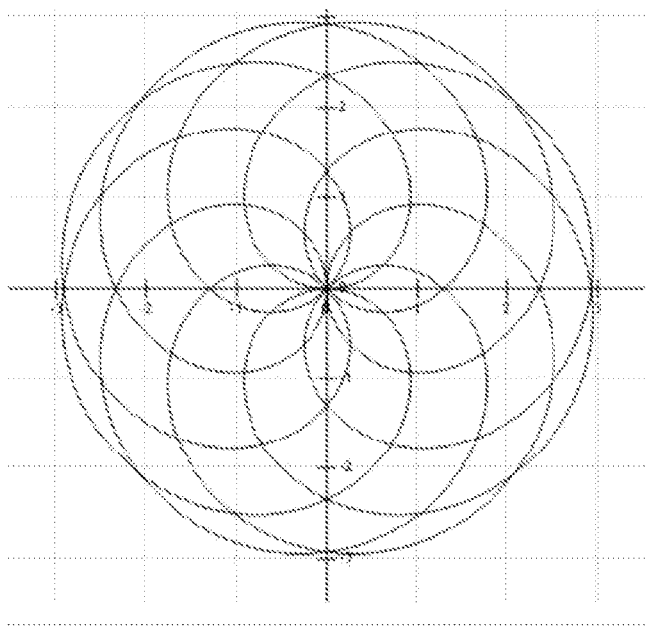
FIG. 4 shows a first embodiment of a scanning pattern in accordance with the invention.

FIG. 4 shows a first embodiment of a scanning pattern in accordance with the invention in a particularly preferred form with B=8 and T=7. From the graph of the function, it is easy to identify that the radius of curvature respectively increases from the edge region toward the center. Moreover, respectively eight points of intersection always lie on a circle concentric with the center of the circumference and the center point is passed through a number of times. Furthermore, it is possible to see from the figure that both the edge region and the region near the center can be measured with a high resolution. The scanning pattern has 48 simple points of intersection and one eightfold point of intersection at the center. The eye movement can be detected and eliminated, particularly by means of the points of intersection away from the center. The high number of points of intersection enables a detection of the eye movement with a correspondingly high frequency (measurement time/number of points of intersection=mean updating time).

Figure 5:
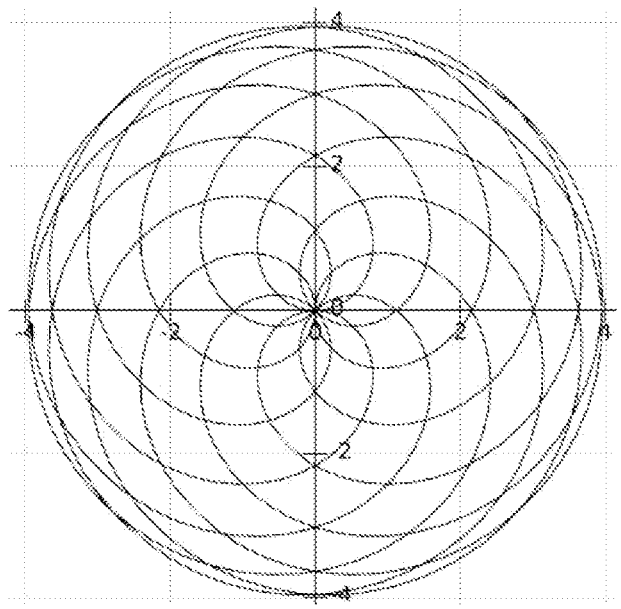
FIG. 5 shows a second embodiment of a scanning pattern in accordance with the invention.

FIG. 5 shows a second embodiment of a scanning pattern according to the invention, where B=8 and T=11. In contrast to the scanning pattern in accordance with FIG. 4, the present scanning pattern has a longer path length and more points of intersection on the same surface. This allows a higher resolution, i.e. shorter mean distances between adjacent measurement points. The number of simple points of intersection is 80 in the present case, with in each case 8 points of intersection per concentric ring.

Figure 6:
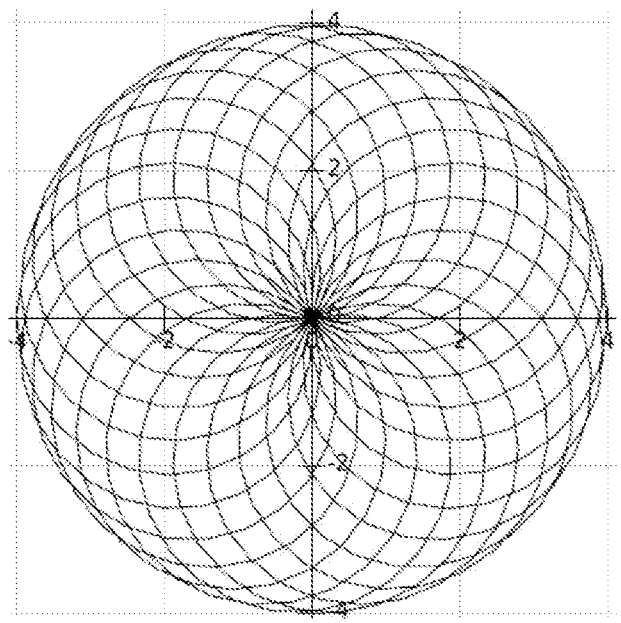
FIG. 6 shows a third embodiment of a scanning pattern in accordance with the invention.

FIG. 6 shows a third embodiment of a scanning pattern according to the invention, where B=13 and T=14. With 26 points of intersection per concentric ring and 13 concentric rings, this embodiment of a scanning pattern has a total of 338 points of intersection. This embodiment, or else those with even more points of intersection, can be used in the case of appropriately fast scanners or for relatively large-area objects. However, the measurement duration along such a trajectory is probably too high using current OCT scanners.

Figure 7:
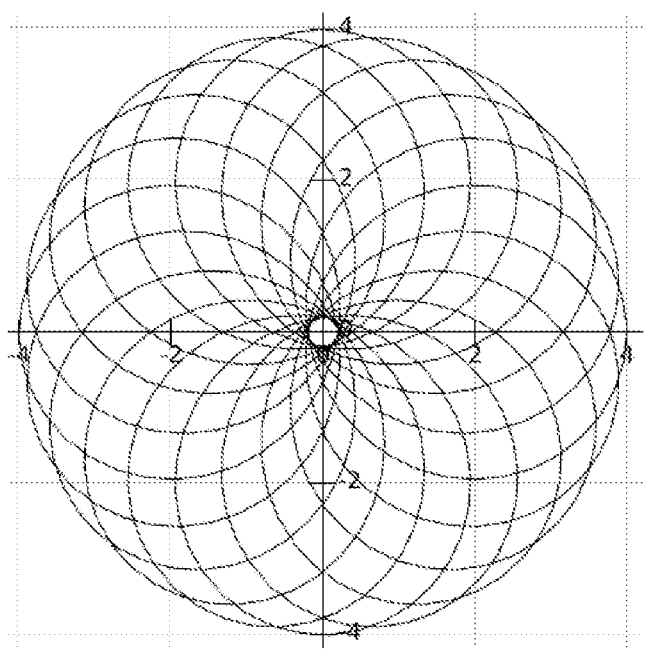
FIG. 7 shows a fourth embodiment of a scanning pattern in accordance with the invention.

Finally, as a fourth example, FIG. 7 shows a hypotrochoid scanning pattern as possible embodiment of a scanning pattern according to the invention. The hypotrochoid scanning pattern has the general form:

$$x(t) = (a-b)\cos(s) + c*\cos\left(\left(\frac{a-b}{b}\right)*s\right);$$
$$y(t) = (a-b)*\sin(s) - c*\sin\left(\left(\frac{a-b}{b}\right)*s\right).$$

However, it is clear to a person skilled in the art that the trajectory in this case is also not restricted to exactly keeping to the graph formed by the equation above. A trajectory or scanning pattern can also deviate from the mathematically exact form. Thus, for example, the set of points established by the measurement beam can merely approximately correspond to such a function as an interpolation.

For establishing measured values in ophthalmology, the values can be selected in such a way that, once again, a radius of approximately 4 mm is obtained. As an example, a=2, b=0.1 and c=2.1 are selected in FIG. 7. Using this parameterization, it is possible to identify a free circle with a radius of approximately 0.2 mm in the center of the circumference. This free surface therefore meets the 0.5 mm criterion set forth at the outset.

In summary, it should be noted that the method according to the invention for registering measurement points can be carried out particularly quickly and it is therefore robust in relation to movements of the body, in particular of the eye, while, simultaneously, a high resolution is achievable, particularly in the edge region of the spherical cap-shaped bodies.

The invention claimed is:

1. Method using a device for registering measuring points on an eye, wherein measurement points are registered by an interferometer along a trajectory on a curved surface of the eye for registering an axial length profile, by way of a measurement beam, wherein the interferometer comprises a controller enabling a guidance of a measurement beam, wherein a minimum radius of curvature of the trajectory is at least ⅐ of a radius of a circumference of the surface, wherein over the whole path length of the trajectory, the trajectory has a maximum radius of curvature which is less than 90% of the radius of the circumference of the surface, and wherein the measurement beam follows a curve with the coordinates $(x(t); y(t)) = (r_0*\sin(\omega_B t)*\cos(\omega_T t); r_0*\sin(\omega_B t)*\sin(\omega_T t))$, where $r_0$ is the radius of the circumference of the surface to be measured and $\omega_B$, $\omega_T$ are angular speeds of the measurement beam's displacement along the projection of the trajectory.

2. Method according to claim 1, wherein at least 90% of the trajectory extends within the circumference.

3. Method according to claim 2, wherein at least 95% of the trajectory extends within the circumference.

4. Method according to claim 2, wherein the whole of the trajectory extends within the circumference.

5. Method according to claim 1, wherein a curvature of the trajectory toward the center of the circumference increases monotonically.

6. Method according to claim 5, wherein a curvature of the trajectory toward the center of the circumference increases strictly monotonically.

7. Method according to claim 1, wherein the trajectory has a point of intersection which is registered at least twice with a time lag.

8. Method according to claim 7, wherein the trajectory has at least two spaced apart points of intersection.

9. Method according to claim 8, wherein the at least two intersections have an angle of intersection which is greater than 90° in the planar projection.

10. Method according to claim 8, wherein the measurement beam follows a trajectory which has more than two points of intersection, wherein, in the case of k*n points of intersection, respectively n points of intersection lie on respectively one of k concentric rings.

11. Method according to claim 10, wherein a distance among two adjacent concentric rings with increasing radius is reduced between three concentric rings with the largest radii.

12. Method according to claim 10 wherein points of intersection between the trajectory and the alternating concentric rings respectively lie on a radially oriented straight line.

13. Method according to claim 8, wherein a point of intersection is registered more than twice with a time lag.

14. Method according to claim 1, wherein the measurement beam is displaced along the projection of the trajectory with a constant angular speed.

15. Method according to claim 1, wherein the measurement points are registered by means of spectral domain OCT or swept source OCT.

16. Method according to one of claims 15, wherein the measurement points are registered with a time-constant frequency.

17. Method according to claim 1, wherein the trajectory is given by loops, wherein adjacent loops intersect.

18. Method according to one of claims 17, wherein two adjacent loops respectively have a point of intersection which lies on a circle concentric with a circumference of the surface to be measured.

19. Method according to claim 1, wherein the trajectory is defined by two frequencies and a radius.

20. Method according to one of claims 19, wherein the trajectory is defined by exactly two frequencies.

21. Method according to claim 1, wherein, for each measurement point on the trajectory, there is a second measurement point on the same trajectory at a distance of less than 25% of the radius.

22. Method according to one of claims 21, wherein, for each measurement point on the trajectory, there is a second measurement point on the same trajectory at a distance of less than 16% of the radius.

23. Method according to claim 1, wherein, for each point within the circumference of the surface, there is a measurement point on the trajectory at a distance of at most 0.5 mm.

24. Method according to one of claims 23, wherein, for each point within the circumference of the surface, there is a measurement point on the trajectory at a distance of at most 0.25 mm.

25. Method according to one of claims 23, wherein, for each point within the circumference of the surface, there is a measurement point on the trajectory at a distance of at most 0.1 mm.

26. Method for approximating a cross section of an eye using measurement points registered by a method according to claim 1, wherein, in a region of a cross section, a subset of registered measurement points, which comprise at least one measurement point at a distance from the cross section, has operations performed thereon in order to approximate the cross section.

27. Method according to claim 26, wherein the subset of the registered measurement points comes from two sectors with center-point angles of less than 90° arranged in a mirror symmetric manner wherein said subset of the registered measurement points is in a circumference of a surface to be measured.

28. Device for carrying out the method according to claim 1.

29. Method according to claim 1, wherein a minimum radius of curvature of the trajectory is at least ⅕ of a radius of a circumference of the surface.

30. Method according to claim 1, wherein a minimum radius of curvature of the trajectory is at least ⅓ of a radius of a circumference of the surface.

31. Method according to claim 1, wherein the point of intersection is registered at least twice with a time lag, as a result of which a movement of the eye is detected.

32. Method using a device for registering measuring points on an eye, wherein measurement points are registered by an interferometer along a trajectory on a curved surface of the eye for registering an axial length profile, by way of a measurement beam, wherein the interferometer comprises a controller enabling a guidance of a measurement beam, wherein a minimum radius of curvature of the trajectory is at least ⅐ of a radius of a circumference of the surface, and wherein the measurement beam follows a curve with the coordinates $(x(t);y(t))=(r_0*\sin(\omega_B t)*\cos(\omega_T t);r_0*\sin(\omega_B t)*\sin(\omega_T t))$, where $r_0$ is the radius of the circumference of the surface to be measured and $\omega_B$, $\omega_T$ are angular speeds of the measurement beam's displacement along the projection of the trajectory.

33. Method using a device for registering measuring points on an eye, wherein measurement points are registered by an interferometer along a trajectory on a curved surface of the eye for registering an axial length profile, by way of a measurement beam, wherein the interferometer comprises a controller enabling a guidance of a measurement beam, wherein a minimum radius of curvature of the trajectory is at least ⅐ of a radius of a circumference of the surface, and wherein the measurement beam follows a curve with the coordinates $(x(t);y(t))=(r_0*\sin(\omega_B t)*\cos(\omega_T t);r_0*\sin(\omega_B t)*\sin(\omega_T t))$, where $r_0$ is the radius of the circumference of the surface to be measured, whereby a mean deviation of the measurement points from the measurement beam is less than 5% and $\omega_B$, $\omega_T$, are angular speeds of the measurement beam's displacement along the projection of the trajectory.

* * * * *